United States Patent
Trent et al.

(10) Patent No.: US 7,416,766 B2
(45) Date of Patent: Aug. 26, 2008

(54) BOTTLES MADE FROM METALLOCENE POLYPROPYLENE FOR DELIVERY OF FRAGRANCES

(75) Inventors: John S. Trent, Franklin, WI (US); Francis J. Randall, Racine, WI (US); Terry M. Kovara, Racine, WI (US); James J. Runkel, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/204,366

(22) Filed: Aug. 16, 2005

(65) Prior Publication Data

US 2007/0042149 A1    Feb. 22, 2007

(51) Int. Cl.
B65D 23/02    (2006.01)
B65D 1/02    (2006.01)
C08F 8/18    (2006.01)

(52) U.S. Cl. ............ 428/35.7; 428/36.7; 428/36.8; 428/36.6; 428/476.1; 428/500; 215/12.2; 525/334.1; 525/355; 525/356; 525/359.1

(58) Field of Classification Search ......... 525/334.1, 525/355, 356, 359.1; 215/12.2; 428/36.6, 428/36.7, 36.8, 36.9, 36.91, 36.92, 476.1, 428/500, 35.7

See application file for complete search history.

(56) References Cited

U.S. PATENT DOCUMENTS

| | | | |
|---|---|---|---|
| 4,314,915 A | 2/1982 | Wiegers et al. | |
| 4,411,829 A | 10/1983 | Schulte-Elte et al. | |
| 4,434,306 A | 2/1984 | Kobayashi et al. | |
| 4,928,881 A | 5/1990 | Barlics et al. | |
| 4,931,230 A | 6/1990 | Krueger et al. | |
| 5,254,378 A | 10/1993 | Krueger et al. | |
| 5,591,395 A | 1/1997 | Schroeder et al. | |
| 5,637,367 A | 6/1997 | Asanuma et al. | |
| 5,647,053 A | 7/1997 | Schroeder et al. | |
| D386,974 S | 12/1997 | Wefler et al. | |
| 5,770,135 A * | 6/1998 | Hobbs et al. | .......... 264/83 |
| 5,811,163 A | 9/1998 | Ohno et al. | |
| 5,840,389 A | 11/1998 | Asanuma et al. | |
| 5,888,636 A | 3/1999 | Asanuma et al. | |
| 5,903,710 A | 5/1999 | Wefler et al. | |
| 5,909,845 A | 6/1999 | Greatbatch et al. | |
| 5,976,503 A | 11/1999 | Martin et al. | |
| 6,123,935 A | 9/2000 | Wefler et al. | |
| 6,223,945 B1 | 5/2001 | Giblin et al. | |
| 6,231,936 B1 | 5/2001 | Kozimor et al. | |
| 6,293,402 B1 | 9/2001 | Rogers et al. | |

(Continued)

FOREIGN PATENT DOCUMENTS

EP    0339413 A2    4/1989

(Continued)

*Primary Examiner*—Roberto Rábago

(57) ABSTRACT

Bottles made of metallocene polypropylene (mPP) for storage and dispensing reservoirs for fragrance compositions, in particular fragrance oils, are described. The mPP bottles can be used in warmer units for slow release dispensing of the fragrance therein. The metallocene polypropylene bottles can be produced by extrusion or injection blow molding, injection molding, injection stretch blow molding (single or two stage), or other suitable molding process. The mPP bottles may optionally have at least one barrier coating layer and/or adhering layer. The mPP bottles may optionally be fluorinated. The mPP bottles have good clarity and possess the required physical properties needed when the bottles are filled on a production line.

8 Claims, 5 Drawing Sheets

U.S. PATENT DOCUMENTS

| | | |
|---|---|---|
| 6,316,547 B1 | 11/2001 | Varlet |
| 6,329,454 B1 | 12/2001 | Krabbenborg |
| 6,537,478 B1 | 3/2003 | Grasmeder et al. |
| RE38,150 E | 6/2003 | Greatbatch et al. |
| 6,645,641 B2 | 11/2003 | Eckstein et al. |
| 6,727,332 B2 | 4/2004 | Demain |
| 6,749,915 B2 | 6/2004 | Tachi et al. |
| 6,750,288 B2 | 6/2004 | Pradel |
| 6,786,427 B2 | 9/2004 | Schram et al. |
| 6,878,761 B2 | 4/2005 | Gugumus et al. |
| 6,890,661 B2 | 5/2005 | Pradel |
| 6,939,919 B2 | 9/2005 | Tau et al. |
| 6,960,375 B2 | 11/2005 | Giblin et al. |
| 7,041,352 B2 | 5/2006 | Barber et al. |
| 7,081,285 B1 | 7/2006 | Barre et al. |
| 7,137,570 B2 | 11/2006 | Wheatley et al. |
| 7,138,474 B1 | 11/2006 | McLeod et al. |
| 7,185,827 B2 | 3/2007 | Quintard et al. |
| 7,186,366 B2 | 3/2007 | Schwinn |
| 7,193,025 B2 | 3/2007 | Maziers et al. |
| 7,220,801 B2 | 5/2007 | Dunaway |
| 7,241,850 B2 | 7/2007 | Burmaster et al. |
| 2001/0048988 A1 | 12/2001 | Forte et al. |
| 2002/0039630 A1 | 4/2002 | Rousselet et al. |
| 2002/0077394 A1 | 6/2002 | Gugumus et al. |
| 2003/0183639 A1 | 10/2003 | Winckels |
| 2003/0209566 A1 | 11/2003 | Winckels |
| 2004/0044106 A1 | 3/2004 | Portnoy et al. |
| 2004/0071456 A1* | 4/2004 | Levine et al. ............... 392/395 |
| 2004/0094468 A1 | 5/2004 | Fritze et al. |
| 2004/0121098 A1 | 6/2004 | Maziers |
| 2004/0152842 A1* | 8/2004 | Dunaway ................... 525/240 |
| 2005/0023185 A1 | 2/2005 | Ramet |
| 2005/0037166 A1 | 2/2005 | Maziers |
| 2005/0045668 A1 | 3/2005 | Winckels |
| 2005/0060953 A1 | 3/2005 | Altonen et al. |
| 2005/0109796 A1 | 5/2005 | Bourque et al. |
| 2005/0142312 A1 | 6/2005 | Giblin |
| 2006/0094810 A1 | 5/2006 | Kim et al. |
| 2006/0105125 A1 | 5/2006 | Musgrave et al. |
| 2006/0111499 A1 | 5/2006 | Kim et al. |
| 2006/0121228 A1 | 6/2006 | Kim et al. |
| 2006/0177616 A1 | 8/2006 | Barber et al. |
| 2006/0269709 A1 | 11/2006 | Maziers |
| 2007/0087214 A1 | 4/2007 | Portnoy et al. |

FOREIGN PATENT DOCUMENTS

| | | |
|---|---|---|
| EP | 0 537 130 B1 | 9/1996 |
| EP | 0902072 A1 | 9/1997 |
| EP | 1 422 249 A1 | 5/2004 |
| EP | 1 169 356 B1 | 7/2004 |
| EP | 1 189 985 B1 | 9/2004 |
| EP | 1495861 * | 1/2005 |
| EP | 1533102 * | 5/2005 |
| EP | 1533102 A1 | 5/2005 |
| WO | WO 2004/106043 A1 | 12/2004 |

* cited by examiner

BOTTLES MADE FROM METALLOCENE POLYPROPYLENE FOR DELIVERY OF FRAGRANCES

FIELD OF INVENTION

The invention relates to bottles made of metallocene polypropylene (mPP) for use as storage and dispensing reservoirs for fragrance-containing compositions, in particular fragrance oils. The bottles of the invention are, in particular, suitable for use in dispensing units for slow release dispensing of fragrances, in particular electric or battery powered warmer units.

BACKGROUND OF INVENTION

Blow-molded flexible containers, injection-molded hollow bodies, films, coatings and sheets made from metallocene polypropylene are known in the art. Fragrance containers made from polypropylene are also known.

For example, known in the prior art is Winckels, U.S. Patent Application Publication No. 2003/0209566 A1, which discloses a packaging product for gel or cream cosmetics. The packaging product has a flexible container or pot and a rigid casing around the pot. The flexible container may be a polypropylene obtained by metallocene catalysis. The rigid structure may be of a thermoplastic material, such as polypropylene.

Also known in the prior art is Winckels, U.S. Patent Application Publication No. 2003/0183639 A1, which discloses a multiple part deformable container for gel or cream cosmetic products wherein the deformable part of the container can be made from metallocene polypropylene.

Also known in the prior art is Eckstein et al, U.S. Pat. No. 6,645,641 B2, which discloses polymeric materials useful in making packaging structures such as films, sheets, lid stocks, pouches, tubes and bags. The structures can be single or multiple layer structures. The layers can be made from propylene catalyzed with a single site catalyst such as metallocene. The dispensing containers disclosed are collapsible.

Also known in the prior art is Winckels, U.S. Patent Application Publication No. 2005/0045668 A1, which discloses a pot for packaging gel or cream cosmetic products. The pot is designed with two dispensing apertures. When the product has a paste-like consistency and does not flow by gravity, preferably the pot includes at least one elastically deformable wall. The deformable wall can be made from a polyolefin obtained by metallocene catalysis, e.g. metallocene polypropylene.

Also known in the prior art is Schram et al, U.S. Pat. No. 6,786,427 B2, which discloses replaceable liquid reservoirs which contain liquids to be dispersed in atomizer devices. The reservoir can be a bottle molded of hard plastic such as polypropylene.

Also known in the prior art is Grasmeder et al, U.S. Pat. No. 6,537,478 B1, which discloses polymers of propylene obtained by metallocene catalysis useful in injection molding various articles.

Also known in the prior art is Dunaway, U.S. Patent Application Publication No. 2004/0152842 A1, which discloses polyolefin blend compositions and products produced therefrom, e.g. blow-molded bottles. The polymer blend composition includes polypropylene and metallocene-produced low density polyethylene. The polypropylene can be produced using any conventional polymerization process with any suitable catalyst, e.g., Ziegler-Natta or metallocene catalyst. Examples of blow-molded containers made with the polymer blend are detergent bottles, soft drink bottles, jars and storage drums. Other articles produced include films, coatings and flexible packaging.

Also known in the prior art is Fritze, U.S. Patent Application Publication No. 2004/0094468 A1, which discloses a freeze resistant water filter. Filter cartridge structures were made of rigid polyolefin polymers such as polypropylene. These polymers, however, are described as becoming brittle in the freezing range. The filter housing is made of an increased elasticity polyolefin polymer, such as metallocene polypropylene.

Also known in the prior art is Gurumus et al, U.S. Patent Application Publication No. 2002/0077394 A1, which discloses a composition containing a polypropylene prepared by polymerization over a metallocene catalyst and a specific hindered amine light stabilizer system.

Also known in the prior art are U.S. Pat. Nos. 5,591,395, 5,647,053, 5,903,710, 5,909,845, 5,976,503, and 6,123,935, which disclose air freshener devices and each, except the '395 patent, disclose that the container or housing of the device can be made of polypropylene.

Also known in the prior art are U.S. Pat. Nos. 4,314,915, 4,411,829, and 4,434,306, which disclose fragrance oil compositions.

Also known in the prior art are U.S. Pat. No. 6,727,332 B2, U.S. Patent Application Publication No. 2004/0044106 A1 and European Patent Application Nos. 1 422 249 A1, 0 537 130 A1, 1 169 356 B1, and 1 189 985 B1, which disclose a preparation of metallocene polypropylene.

SUMMARY OF INVENTION

The invention involves bottles made of metallocene polypropylene (mPP) useful as storage and dispensing reservoirs for fragrance-containing compositions, and in particular fragrance oils. The bottles of mPP are especially suitable for use in dispensing units for slow release dispensing of the fragrances, in particular electric or battery powered warmer units.

More particularly, preferred embodiments of the invention relate to bottles made of mPP that hold fragrance oil which are inserted into dispensing units, which are preferably warmer units connected to a power source, e.g., an electrical wall outlet, car power jack, battery, or the like. The mPP bottles of the invention are particularly useful for containing compositions including fragrance oils since fragrance oils will permeate into many polymer structures and break the polymer down resulting in leakage which means loss of product and possible damage to adjacent surrounding materials. The bottles of the invention have a rigid structure. The invention relates to polypropylene resins produced using a metallocene single site catalyst. Traditionally, polypropylene resins are produced from a Ziegler-Natta multiple site catalyst. The mPP bottles are produced by blow molding, injection molding or any other suitable molding process. The mPP bottles may optionally have at least one barrier coating layer and/or adhering layer. The one or more barrier coating layers may be on the inside and/or outside the body of the bottle, the body understood to include interior walls and exterior walls.

Metallocene polypropylene rigid bottles have shown unexpectedly good results in weight loss tests, have good clarity and possess the required physical properties needed when the bottles are filled on a production line.

A better understanding of these and other aspects, features and advantages of the invention may be had by reference to the drawings and to the accompanying description, in which preferred embodiments of the invention are illustrated and described.

BRIEF DESCRIPTION OF THE DRAWINGS

Referring to the drawings.

DETAILED DESCRIPTION OF THE INVENTION

Figure 1:
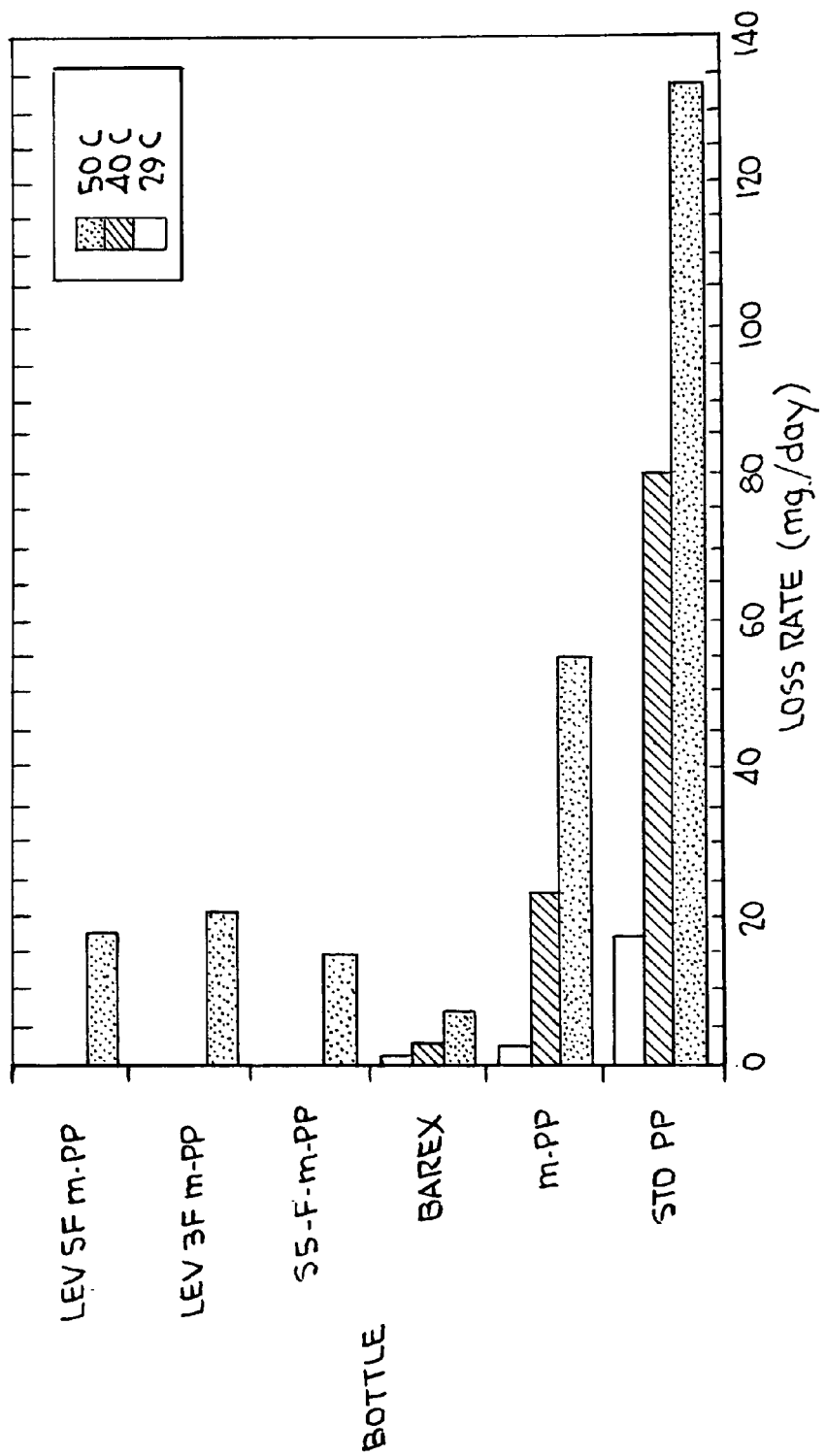
FIG. 1 shows the effect of bottle plastic on fragrance (Mandarin) loss rate.

The invention relates to bottles made of metallocene polypropylene (mPP) useful as storage and dispensing reservoirs for fragrance-containing compositions, in particular fragrance oils. The fragrance-containing compositions are for providing scent to surrounding atmosphere, but may contain one or more additional components, such as a carrier (e.g., water, alcohol or the like) or active ingredient (e.g., a bactericide, such as triethylene glycol, or the like). The invention especially relates to bottles of mPP that hold fragrance oils. Fragrance oils are particularly problematic for long term storage and dispensing since fragrance oils will go into the polymer of a storage bottle and break the polymer down resulting in leakage. Leakage is necessarily detrimental due to loss of product and damage to surrounding surfaces or materials. The bottles of the invention have a rigid structure and are particularly useful in dispensing units for providing slow release dispensing of the fragrance. The invention relates to polypropylene resins produced using a metallocene single site catalyst. Traditionally, polypropylene resins are produced from a Ziegler-Natta multiple site catalyst. The mPP bottles are formed by conventional blow molding, injection molding or any other suitable means as further described hereafter. The mPP bottles may optionally have at least one barrier coating layer and/or adhering layer.

As described below, the mPP resin bottles of the invention have been found to unexpectedly provide advantageous storage for fragrance oils and use upon insertion into warmer dispensing units which provide slow release dispensing upon connection to a suitable power source, such as an electrical wall outlet, battery, or the like. However, the mPP resin bottles may be useful for other rigid container purposes requiring prolonged storage of fragrances. For discussion purposes and in view of the specific examples set forth below, the mPP bottles will be further described herein in relation to storing and dispensing fragrance oils.

The mPP bottles of the invention provide unexpected advantages with respect to being a storage and dispensing reservoir for fragrance oils as shown by the good results in weight loss tests, its good clarity and possession of the required physical properties needed when the bottles are filled on a production line. These products and properties are detailed hereafter.

The mPP resins made from a metallocene single-site catalyst, instead of traditional polypropylene resins made from Ziegler-Natta multiple site catalyst (ZNPP), can be effectively used to make rigid bottles that hold fragrance oils in storage and dispensing. Bottles made from mPP resin can replace current bottles for fragrance oils made from more costly resins, such as Barex® 210 and 218, which are acrylonitrile (AN)-methyl acrylate (MA) copolymers grafted onto nitrile rubber and marketed by Innovene (a subsidiary of BP Chemicals).

Metallocene polypropylene resins are manufactured by a number of suppliers that include Dow Chemical, ExxonMobil, Basell, and Total Petrochemicals USA, Inc. The mPP made by Total has a desired molecular weight and melt flow as detailed below and therefore is especially suitable for automated production. In a preferred embodiment, for example, mPP bottles are fabricated by an injection blow molding (IBM) process and/or extrusion blow molding (EBM) process using Total M3282MZ resin manufactured by Total Petrochemicals USA, Inc. These mPP bottles performed unexpectedly well in weight loss tests, have good clarity, and possess the required physical properties (i.e., top load strength, flexural modulus strength and impact resistance) needed when filling the bottles with scented oil fragrances on production lines.

Metallocene polypropylene resins generally have narrow molecular weight distributions with extremely low levels of extractables. The molecular weight of mPP resins is generally measured by the melt flow of the resin. More particularly, as the molecular weight of the mPP resin increases or decreases, the melt flow of the mPP resin changes. Specifically, as the molecular weight of the mPP resin increases, the melt flow of the mPP resin decreases and vice versa. In a preferred embodiment of the invention, the mPP resin has a melt flow of about 1 g/10 min. to about 10 g/10 min. for the EBM process and about 1 g/10 min. to about 40 g/10 min. for the IBM process. However, the melt flow of the mPP resin of the invention can be in a range of from about 0.5 g/10 min. to about 50 g/10 min., more preferably from about 1 g/10 min. to about 30 g/10 min. and most preferably from about 1 g/10 min. to about 20 g/10 min. for all types of blow molding processes.

The mPP resin bottle of the invention may be made by blow molding, injection molding or any other suitable molding process (i.e., single stage or two stage injection stretch blow molding (ISBM) process). For extrusion blow molding, an mPP resin having a melt flow from about 0.5 g/10 min. to about 5 g/10 min. is preferred. For injection blow molding, an mPP resin having a melt flow from about 1 g/10 min. to about 20 g/10 min. is preferred to provide the required strength and enhanced barrier properties of the mPP resin. In terms of performance, the mPP bottles of the invention have the same desired properties and provide the same data results upon testing regardless of the method of molding. Any conventional molding process may be used to make the mPP resin bottles of the invention to provide the desired results.

A clarifying agent or nucleating agent is conventionally added to polypropylene during manufacture because polypropylene is naturally cloudy and the addition of a clarifying agent or nucleating agent increases clarity and stiffness of the resin. A clarifying or nucleation agent is preferably added to the polymer in very small amounts causing increases in crystallization rates of the polypropylene to change so that the crystalline structures formed, called spherulites, are smaller and more numerous than the un-nucleated polypropylene. Clarity is enhanced due to the decreased spherulite size, which reduces the scattering of light as it passes through the material.

Clarified mPP is used in the tests as described below to show the advantages of the invention because manufacturers currently add a clarifying agent and do not provide a commercially available mPP resin made with a nucleating agent in the melt flow range of interest. However, the mPP resins may be used if desired without a clarifying agent or nucleating agent that will provide the same physical strength and barrier property results, but possess poor clarity.

In a preferred embodiment of the invention, the mPP resin bottles are made of mPP alone. Results have shown that mPP alone in these bottles provides adequate barrier properties. However, in another embodiment, as shown for example in FIGS. 7 and 8, the bottles may optionally have a barrier coating as a layer on the inside wall and/or outside wall of the bottle to enhance barrier properties in situations requiring an extra barrier due to the nature of the particular fragrance oil. These enhanced barrier properties include having a use/storage temperature above 50° C., preventing permeation of fragrances/composition from the bottle, preventing oxygen permeation into the bottle, and reducing migration of water into the bottle from the atmosphere.

In comparison to the mPP resin of the invention, other resins provide good barrier properties also, such as Barex® resin, but are expensive. Certain resins also have other disadvantages/problems when used for holding fragrance oils due to permeation of fragrance and/or oxygen through the material or causing rapid deterioration of physical properties (i.e., environmental stress cracking issues).

In another embodiment, the mPP resin bottles may have a thin film on the walls of the bottle, such as an adhering layer, to join a barrier coating to the mPP bottle. The mPP bottle of the invention provides enhanced barrier properties with or without a barrier coating layer. Accordingly, a preferred embodiment of the mPP bottles of the invention does not have a barrier coating on the interior wall or exterior wall of the mPP bottle. As such, the mPP bottles can be manufactured without using special coating procedures to apply a barrier coating involving the use of a solvent and stripping of the solvent. However, the mPP bottles may optionally have a barrier coating layer with or without an adhesive layer.

Accordingly, the mPP resin bottles of the invention provide enhanced barrier properties such as preventing permeation and therefore preventing loss of product, permeation of oxygen into the bottle that could cause unwanted oxidation of certain fragrance components, or preventing weight gain due to permeation of water into the bottle. Additional enhanced barrier properties of the mPP bottles include good clarity and predetermined physical properties of the bottles for delivery of fragrance oils. These predetermined physical properties include, but are not limited to, increased top load strength, flexural modulus strength, and impact resistance.

The mPP bottles may also be fluorinated such as by exposure to fluorine gas. Fluorination improves barrier properties against fragrance permeation. Fluorination, however, does not significantly reduce oxygen permeation. Fluorination is described further below in relation to the examples.

Components of the mPP resin bottle detailed above and as referred to in the examples set forth below are shown in Table 1. Table 1 includes components (chemical name and common/commercial name), and the weight percent, type and function of each component.

TABLE 1

| Weight Percent | Common name or commercial name | Chemical | Type | Function |
| --- | --- | --- | --- | --- |
| 100-51% | Total M3282MZ | Metallocene Homopolymer Polypropylene with Clarifier | Polymer | Bottle Material |
| 0-100% | Barex ® 210 or 218 | Acrylonitrile (AN) - methyl acrylate (MA) copolymer grafted onto nitrile rubber | Polymer | Barrier Coating to Bottle Material |
| 0-5% | Fluorination | Fluorine | Surface Modifier | Barrier Coating on mPP Bottles |
| 0-10% | PAN | Polyacrylonitrile | Surface Modifier | Barrier Coating on mPP Bottles |
| 0-1% | Eastman ™ Adhesion Promoter 550-1 | | Surface Modifier | Adhesive Layer for mPP Bottle Coatings |
| 0-10% | Nylon 6 or 66 | Polyamides | Surface Modifier | Barrier Coating on mPP Bottles |
| 0-10% | PET, PTT, PCT, PEN PETG, PCTG, or PCTA | Polyesters (homopolymers and copolymers) | Surface Modifier | Barrier Coating on mPP Bottles |
| 0-10% | PVDC or PVC | Polyvinylidene chloride or polyvinyl chloride | Surface Modifier | Barrier Coating on mPP Bottles |

The examples that follow are intended to illustrate the invention and not to limit the invention.

The following illustrates the surprising performance difference between mPP and ZNPP polymers when exposed to typically used fragrances in the form of oils.

EXAMPLE 1

Chemical Resistance of Metallocene Homopolymer Polypropylene vs. Zeigler-Natta Random Copolymer Polypropylene Towards Fragrance Oil Components as Shown by Swell Tests Weighed samples of two polypropylene types (1) Total M3282MZ (clarified mPP resin) and (2) Total NO3112-2 (NA21 nucleated Zeigler-Natta random copolymer polypropylene designated below as ZN-RCPP) were placed in vials containing samples of forty fragrance components typically used to formulate various fragrances. Both of these polypropylene resins were supplied by Total Petrochemicals USA, Inc. All samples were placed in an environmental chamber at 85° F. (29.4° C.) for two weeks and then removed, paper towel dried and weighted. Weight gains were calculated and results are shown in Table 2.

TABLE 2

Percent Weight Gains of Polypropylene Samples
After 2 Weeks By Immersion @ 85° F.: mPP versus ZNPP

| Sample | Fragrance Component | M3282MZ % Swelling | Note | ZN-RCPP % Swelling | Note |
|---|---|---|---|---|---|
| 1 | Aldehyde MNA | 1.27% | | 5.74% | |
| 2 | Allyl Amyl Glycolate | 1.37% | | 3.19% | |
| 3 | Applinal | 0.62% | | 1.41% | |
| 4 | Benzyl Acetate Extra | 1.92% | | 2.57% | |
| 5 | Benzyl Alcohol | 0.60% | | 0.50% | |
| 6 | Benzyl Propionate | 2.59% | | 3.53% | |
| 7 | Camphor White | 5.04% | warped | 14.52% | warped |
| 8 | Carbitol | 0.62% | | 0.60% | |
| 9 | Cineol | 1.37% | | 15.29% | warped |
| 10 | Citrolellol | 0.56% | | 0.79% | |
| 11 | Clove Leaf Oil | 1.31% | | 2.32% | |
| 12 | Cyclamen Aldehyde | 0.88% | | 2.07% | |
| 13 | Diethyl Malonate | 1.22% | | 0.92% | |
| 14 | Dihydromyrcenol | 5.27% | | 0.77% | |
| 15 | Dow DPM | 0.78% | | 0.78% | |
| 16 | Eucalyptus Oil | 2.02% | | 14.02% | warped |
| 17 | Eugeneol rectified | 0.86% | | 1.83% | |
| 18 | Florocyclene | 1.53% | | 4.47% | warped |
| 19 | Geraniol | 0.69% | | 0.36% | |
| 20 | Geranyl Acetate | 2.03% | | 4.64% | |
| 21 | Grapefruit Oil | 12.07% | | 12.55% | warped |
| 22 | Hexyl Acetate | 7.78% | | 6.75% | warped |
| 23 | Hexyl Cinnamic Aldehyde | 1.14% | | 1.43% | |
| 24 | Isobornyl Acetate | 0.87% | | 2.31% | |
| 25 | Jasmacylene | 1.36% | | 3.84% | warped |
| 26 | Lavandin Oil | 0.99% | | 2.05% | |
| 27 | Lavender Oil | 1.23% | | 3.57% | warped |
| 28 | Ligustral | 2.27% | | 8.02% | |
| 29 | Lilial | 0.61% | | 1.06% | |
| 30 | Linalool | 0.69% | | 1.68% | |
| 31 | Linalyl Acetate | 0.75% | | 2.36% | |
| 32 | Orange Florida | 12.00% | warped | 13.42% | warped |
| 33 | Orange Terpenes | 10.94% | warped | 13.72% | warped |
| 34 | Ortholate | 0.48% | | 1.94% | |
| 35 | Peppermint Oil | 1.04% | | 6.02% | warped |
| 36 | Phenylethanol | 0.52% | | 0.13% | |
| 37 | PTBCHA | 1.04% | | 3.32% | warped |
| 38 | Terpineol alpha | 0.92% | | 1.16% | |
| 39 | Terpinyl Acetate | 1.28% | | 3.04% | warped |
| 40 | Allyl heptanoate | 6.63% | | 7.05% | |

As shown in Table 2, weight gains by the M3282MZ mPP resin were significantly lower overall than ZN-RCPP resin. Table 2 also indicates where physical distortion of the polypropylene sample occurred. Greater than 10% weight gain was observed for grapefruit oil, orange terpenes, and orange florida for both polypropylene type samples. Grapefruit oil, orange terpenes and orange florida all contain high levels of D-limonene (grapefruit 90%, orange terpenes 94%), which is soluble in polypropylene. Additionally, greater than 10% weight gain was also observed for the ZN-RCPP samples exposed to camphor white, cineol, and eucalyptus oil. Camphor is a solid melting at 175° C. and white camphor oil contains cineol, camphor, borneol, camphene, menthol, borneol, pinene and dipentene. Dipentene is chemically the same as limonene, except that it contains both the D and L optical isomers. Therefore, swelling is probably due to the dipentene and pinene content. Eucalyptus oil is about 70-80% cineol, but also contains camphene, citronellal, fenchene and phellandrene. Since both cineol and eucalyptus oil swells polypropylene, cineol is probably the agent causing the swelling.

Accordingly, most of the fragrance components in Table 2 do not appear to cause significant swelling of samples made of mPP. The exceptions are fragrance oils that contain high levels of limonene. Cineol and perhaps dipentene and pinene are also a problem. Consequently, fragrances should not contain large amounts of the types of fragrance components that are soluble in polypropylene when it is desirable to use polypropylene bottles or, alternatively, barrier coating(s) are applied to the bottle in order to enhance the barrier properties of the bottle. Many of the chemical structures for the fragrance components in Table 2 are below. The number of the chemical structure below corresponds to the sample number of the fragrance component in Table 2.

(1)

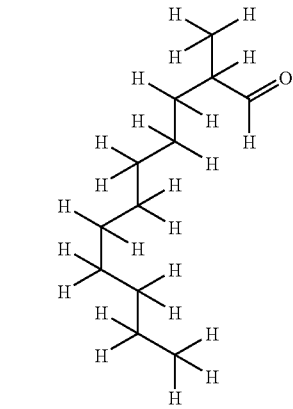

(2)

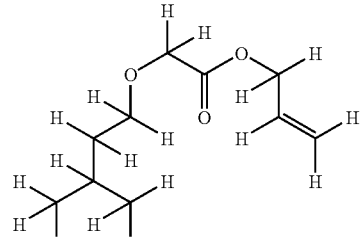

(3)

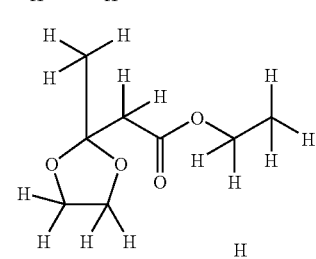

(4)

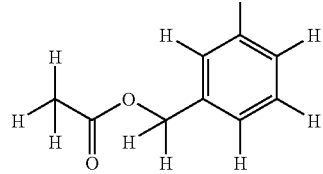

(5)

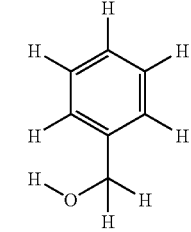

-continued
(6)
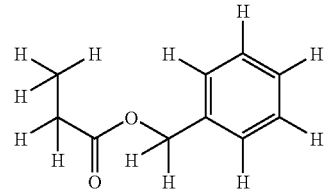
(7)
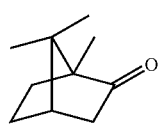
(8)
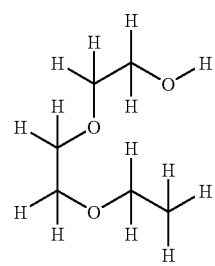
(9)
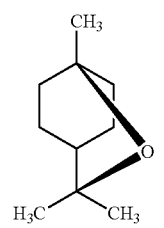
(10)
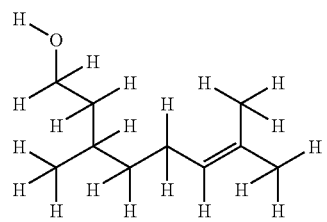
(12)
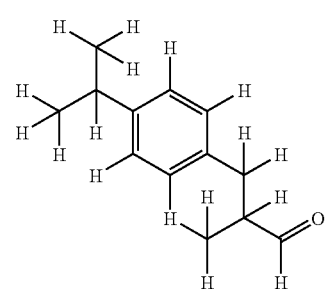
(13)
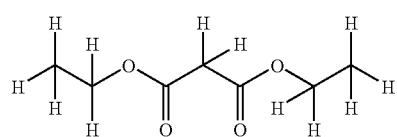
-continued
(14)
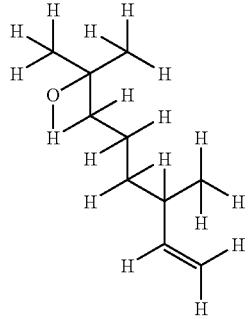
(15)
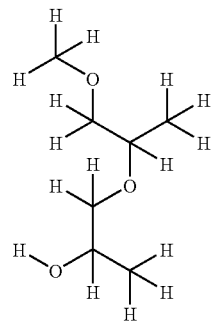
(17)
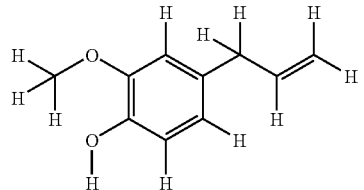
(19)
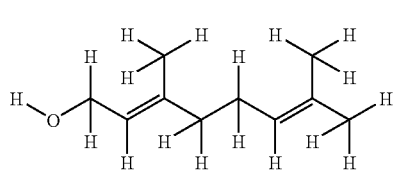
(20)
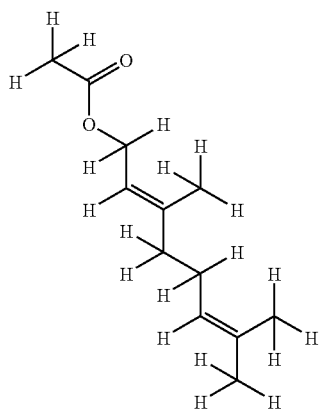

-continued
(22) 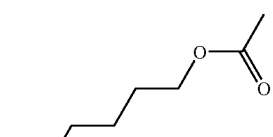
(23) 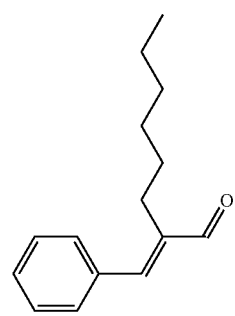
(24) 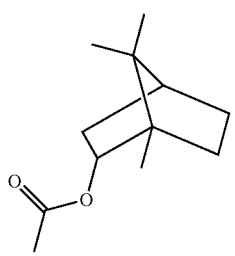
(25) 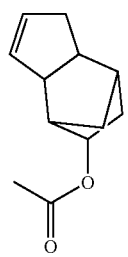
(28) 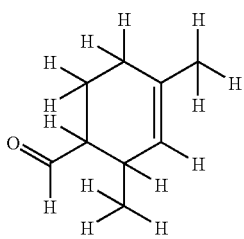
(29) 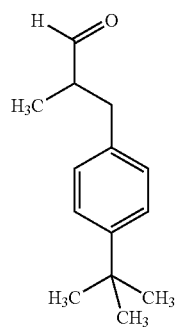
-continued
(30) 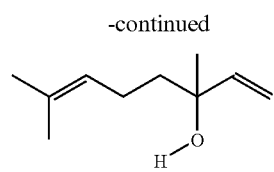
(31) 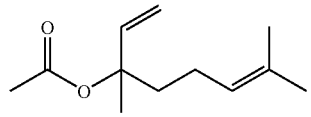
(33) 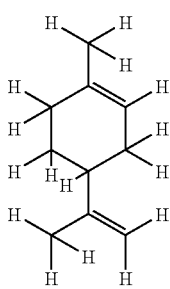
(34) 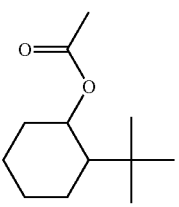
(36) 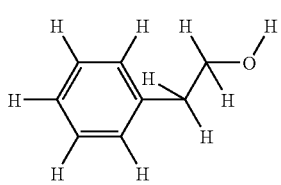
(37) 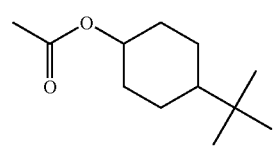
(39) 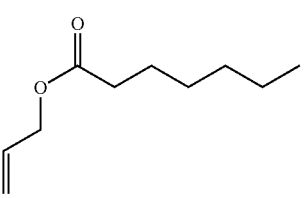
(40) 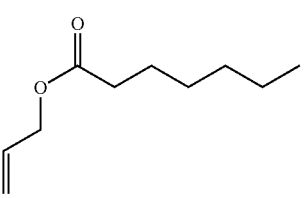

EXAMPLE 2

Chemical Resistance of Metallocene Homopolymer Polypropylene vs. Ziegler-Natta Random Copolymer Towards Mandarin Fragrance Oil as Shown by Weight Loss Tests Mandarin fragrance, which is no longer marketed by Changing Paradigms in ZN-RCPP bottles due to leakage and high fragrance migration issues associated with the bottle, contains approximately 30% limonene. Consequently, this fragrance was chosen because of its aggressive nature to migrate through polypropylene and to demonstrate how different metallocene polypropylene resins compare to Ziegler-Natta catalyzed random copolymer polypropylene resins that are commercially used to make fragrance bottles. Table 3 shows the weight loss results after 113 days when 25 grams of Mandarin fragrance was held in fragrance bottles made out of ZN-CRPP, mPP and Barex® 210 resin (acrylonitrile methyl acrylate copolymer grafted onto nitrile rubber). Barex® 210 is the material currently used for holding fragrance oils and dispensing of such oils using various kinds of electric warmer units. The ZN-RCPP is a random copolymer containing approximately 5% ethylene comonomer content. The mPP is a metallocene homopolymer polypropylene with the tradename Total M3282MZ resin. In addition, some of the fabricated mPP bottles were fluorinated to three different levels (i.e., level 3, level 5 and super level 5) as designated by Fluoro-Seal International so that testing could be done to determine if surface modifications to both the inside and outside walls of the mPP bottles could effectively reduce permeation of the more soluble fragrance components such as linonene, camphor white, orange florida, orange terpenes and allyl heptanoate (see Table 2 where these fragrance components caused warpage in mPP samples). These samples were fluorinated by Fluoro-Seal International by exposing the mPP bottles to fluorine gas. While fluorination improved barrier properties against fragrance permeation, fluorination did not reduce oxygen permeation.

TABLE 3

Weight Loss Comparison of Mandarin Fragrance In Various Bottles

| Fragrance Source | Fragrance ID | Bottle Material | Rate of Weight Loss (mg/day) | | |
|---|---|---|---|---|---|
| | | | 50° C. (122° F.) | 40° C. (104° F.) | 29° C. (84° F.) |
| Chg. Paradigms | Mandarin | ZN-RCPP | 133.5 | 80.0 | 17.0 |
| Chg. Paradigms | Mandarin | mPP | 55.0 | 23.0 | 2.3 |
| Chg. Paradigms | Mandarin | Barex ® 210 | 7.0 | 2.8 | 0.7 |
| Chg. Paradigms | Mandarin | Super 5 $F_2$ mPP | 14.7 | | |
| Chg. Paradigms | Mandarin | Level 3 $F_2$ mPP | 21.1 | | |
| Chg. Paradigms | Mandarin | Level 5 $F_2$ mPP | 18.3 | | |

The weight loss of Mandarin fragrance sealed in fragrance bottles equipped with wicks and caps at three different temperatures were monitored for almost four months. Weight loss became constant after two weeks and reproducibility between replicates was found to-be good. The Barex® units have lower loss rates than any of the polypropylene units, as expected in view of its current preferred choice as a fragrance oil bottle. Barex® 210 resin, however, is expensive and, thus, a material having comparative properties as an alternative is highly desirable. The results of Table 3 clearly show that mPP bottles provide a much lower loss rate than ZN-RCPP bottles. In addition, fluorination of mPP bottles reduced the rate of loss of Mandarin fragrance to even lower degrees. This effect in loss rate is shown for example in FIG. 1 which graphically shows the effect of bottle plastic on Mandarin fragrance loss rate. Accordingly, it is possible to approach the performance of Barex® bottles through the combination of using mPP resins to fabricate fragrance bottles and surface modification by fluorination.

EXAMPLE 3

Figure 2:
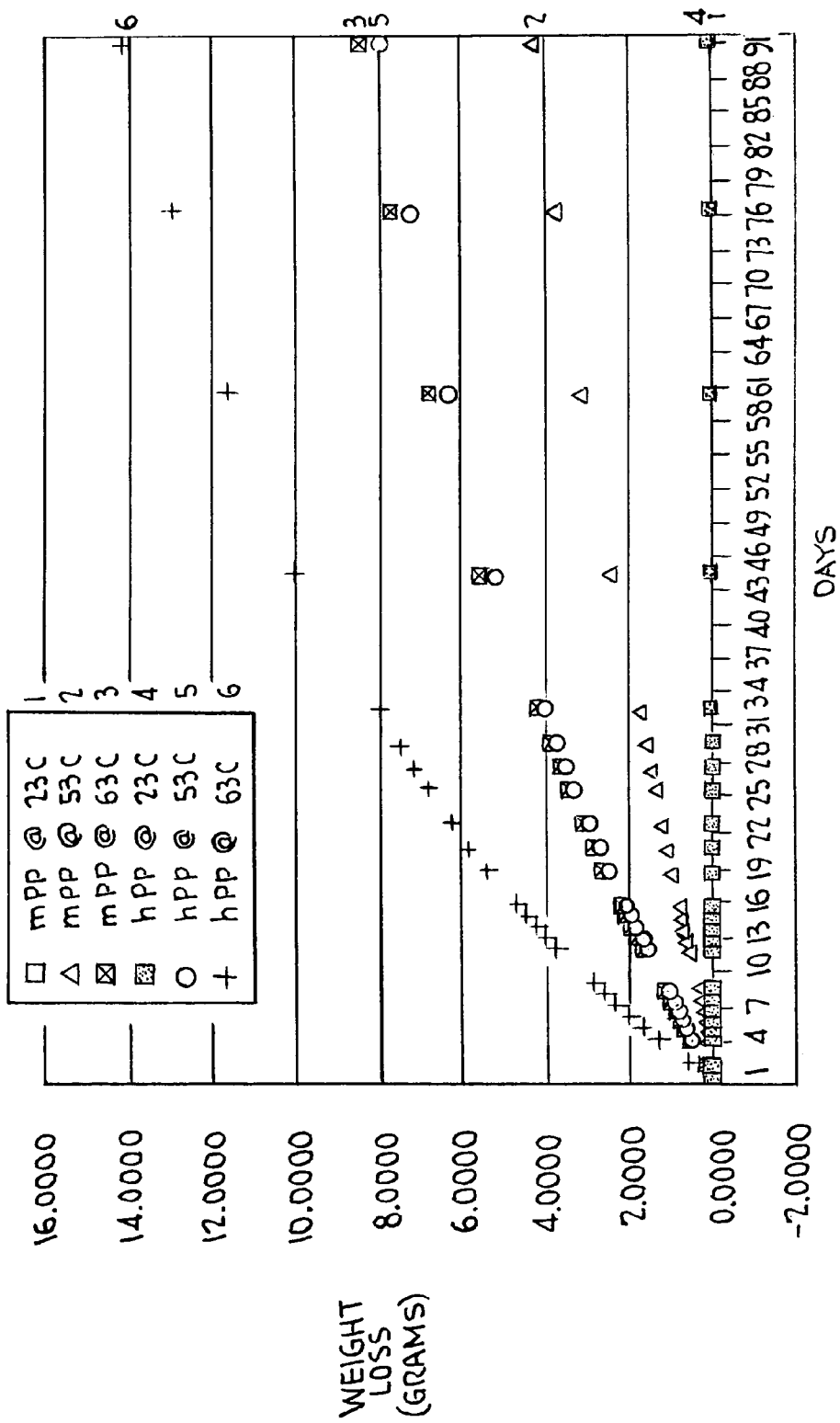
FIG. 2 shows weight loss results for a fragrance (Hawaiian Breeze) in various polypropylene bottles at differing temperatures.

Chemical Resistance of Metallocene Polypropylene vs. Ziegler-Natta Random Copolymer Polypropylene Towards Hawaiian Breeze Fragrance Oil Shown by Weight Loss Tests Thin walled one-ounce polypropylene bottles were made by Monarch Plastics Limited by the extrusion blow molding (EBM) process using Total M3282MZ (clarified mPP) and Total M3132-2 (NA21 nucleated Ziegler-Natta random copolymer polypropylene designated as "hPP" hereafter and in FIG. 2) resins supplied by Total Petrochemicals USA, Inc. To these bottles were added 40 grams of Hawaiian Breeze fragrance, manufactured by Takasago International Corporation. Afterwards all filled bottles were induction sealed, tightly capped and weighed prior to temperature exposure to 23° C. (73.4° F.), 53° C. (127.4° F.) and 63° C. (145.4° F.) Weight loss measurements were taken over a 91 day period and the results are shown graphically in FIG. 2. Both types of polypropylene bottles completely contain Hawaiian Breeze fragrance when exposed to room temperature (23° C.). By increasing the temperature to 53° C. and 63° C., a performance difference between metallocene and Ziegler-Natta polypropylene can be more clearly seen. After 91 days, weight loss of Hawaiian Breeze in hPP bottles is 2 times that found in mPP bottles at 53° C., and 1.7 times at 63° C.

EXAMPLE 4

Enhancing the Chemical Resistance of Metallocene Polypropylene Bottles Towards Hawaiian Breeze and Mandarin Fragrance Oils by Dip Coating Preparation of Dipping Solutions: Barex® 210 resin was dissolved in dimethyl formide (DMF) to three different weight percent levels of 3%, 7% and 10%, designated as Solutions A, B and C, respectively. In addition, a 1.6% by weight solution of Eastman™ Adhesion Promoter 550-1 in xylene (Solution D) was prepared in order to modify the mPP bottle surfaces (inside and out) so that the coatings applied from Solutions A, B and C would effectively adhere to the mPP surfaces.

Dip Coating Process: The first step in the bottle coating process was to dip mPP bottles into Solution D heated to 50° C., drain the bottles completely of solution and permit them to dry first in air for 1 hour, then in a vacuum oven set at 55° C. for 1 hour to complete the drying process. Then sets of dried Solution D coated mPP bottles were dipped separately into Solutions A, B and C where each solution was heated to 95° C. prior to dipping. Once the bottles were dipped in Solutions A, B or C, they were drained of solution and allowed to dry in air for 1 hour and then in a vacuum oven set at 55° C. for 12-20 hours. The bottles were then filled with Hawaiian Breeze and Mandarin fragrance oils to perform weight loss experiments conditioned at 50° C. Filled Barex® bottles and uncoated mPP bottles served as controls, and were compared to Barex® coated mPP bottles from Solutions A, B and C.

Figure 3:
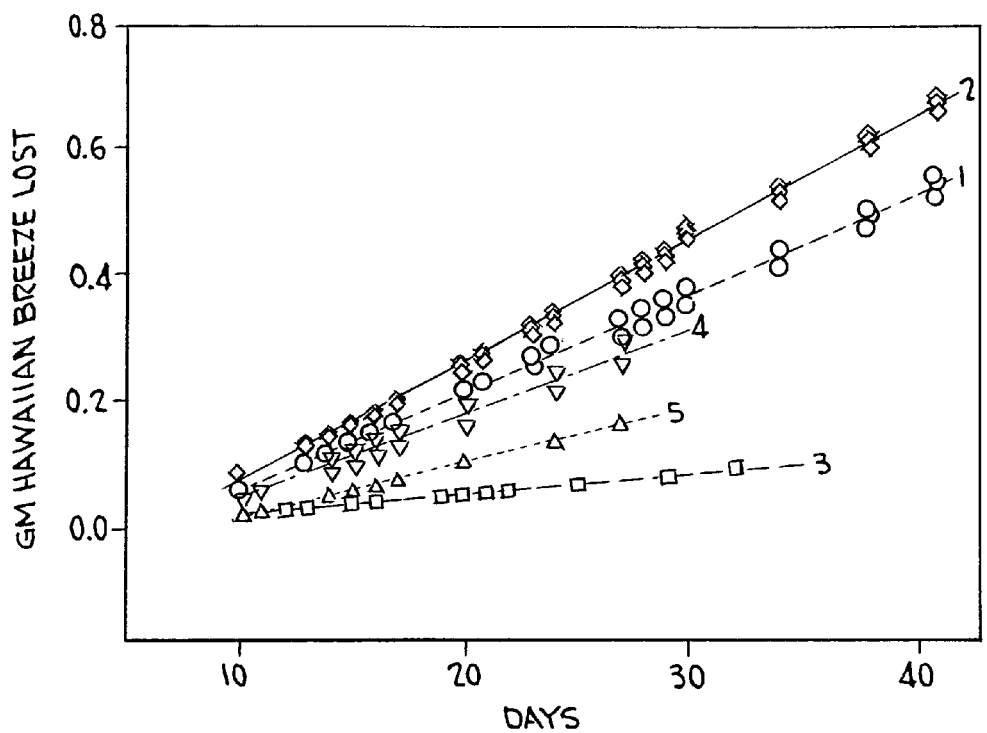
FIG. 3 shows the effect of bottles of different plastics on weight loss of Hawaiian Breeze fragrance at 50° C.
Figure 4:
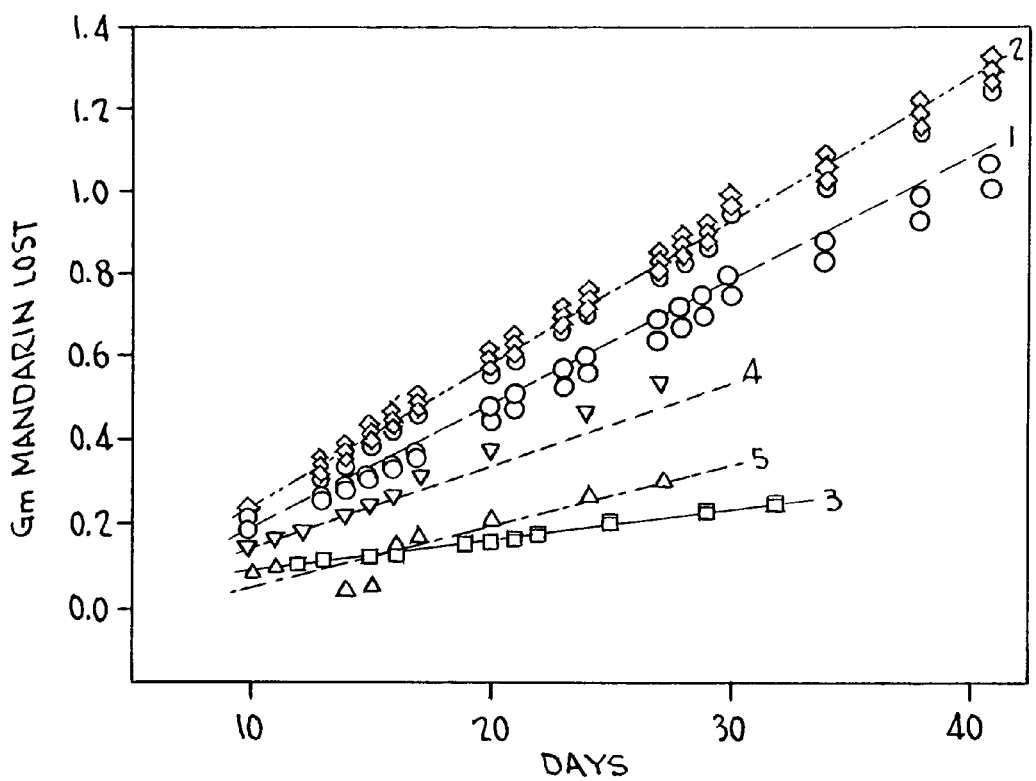
FIG. 4 shows the effect of various bottles under different conditions on weight loss of Mandarin fragrance at 50° C.

Weight Loss Experimental Results: FIGS. 3 and 4 show the weight loss results (two test bottles per condition) after 45 days of Barex® coated mPP bottles compared to Barex® and uncoated mPP bottles filled with Hawaiian Breeze and Mandarin fragrance oils, respectively. Both FIGS. 3 and 4 show that the application of a barrier layer such as Barex® 210 resin can effectively reduce the permeation rates of fragrance oils through the walls of the mPP bottle quite significantly. Increasing the barrier coating thickness by dip casting from a 3% to 7% to 10% solutions, progressively reduced weight loss which approached the weight loss values of bottles made from 100% Barex® 210 resin.

EXAMPLE 5

Chemical Resistance of Metallocene Polypropylene Towards Various Fragrance Oils Shown by Weight Loss Tests Uncoated mPP and Barex® bottles were filled with six fragrance oils made by Takasago International Corporation and Quest Internation in order to conduct weight loss studies with time at room temperature. Table 4 shows that there is virtually no weight loss of these fragrance oils over a six month period, but rather a weight gain due to water vapor migration into the bottle. With respect to water uptake, the mPP bottles outperformed the Barex® bottles.

TABLE 4

Six Month Weight Loss/Gain Test of Sealed mPP versus Barex ® Bottles Conditioned at Room Temperature

| Fragrance | mPP RT (72° F.) 6 Months | Barex ® RT (72° F.) 6 Months |
|---|---|---|
| Hawaiian Breeze | (+) 0.006 g/.024% | (+) 0.029 g/.104% |
| Refreshing Spa | (+) 0.026 g/.093% | (+) 0.136 g/.482% |
| Vanilla Breeze | (+) 0.016 g/.057% | (+) 0.265 g/.934% |
| Rainshower | (+) 0.029 g/.102% | (+) 0.104 g/.367% |
| Apple Cinnamon | (+) 0.015 g/.054% | (+) 0.209 g/.738% |
| Clean Linen | (+) 0.032 g/.114% | (+) 0.287 g/1.01% |

The mPP bottles of the invention may be tinted with a pigment in varying amounts to provide various shades of tinted bottles or may have no pigment and therefore no tint.

The mPP resin preferably used to make the bottles in the examples is Total Polypropylene M3282MZ, manufactured by Total Petrochemicals USA, Inc. as detailed above. M3282MZ has the following properties: a melt flow index of 2.3 g/10 min.; density of 0.905 g/cc; melting point of 307° F. (153° C.); tensile strength of 4,900 psi (33.8 MPa); elongation of 72%; and a flexural Modulus of 216,000 psi (1,490 MPa).

Metallocene homopolymer polypropylenes can preferably be used in a melt flow range of 0.5 to 50 g/10 min., more preferably in the range from 1 to 30 g/10 min., and most preferably from 1 to 20 g/10 min. as detailed above. When bottle strength is not considered a critical parameter, metallocene copolymer polypropylenes having the same melt flow ranges of that provided for the metallocene homopolymer polypropylenes may be used.

Figure 5:
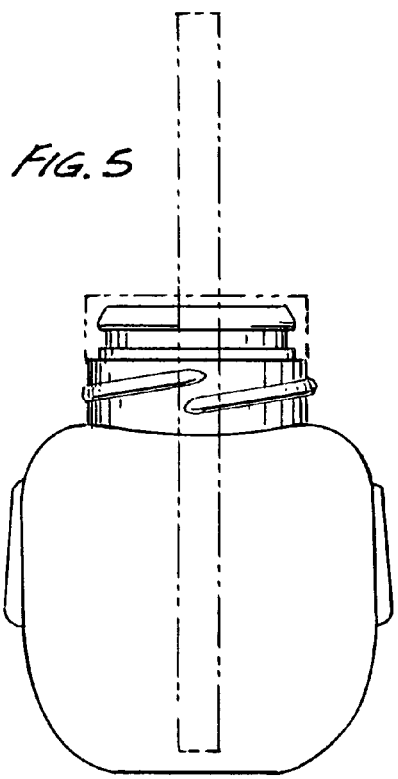
FIG. 5 shows a side view of an embodiment of a bottle of the invention, including the presence of a wick therein.
Figure 6:
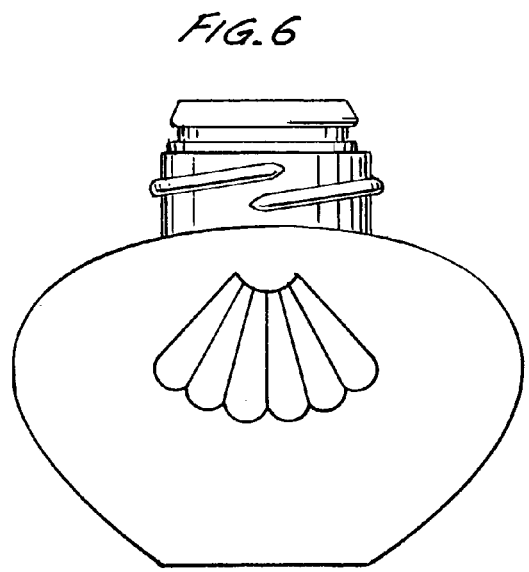
FIG. 6 shows a front view of an embodiment of a bottle of the invention.

FIGS. 5 and 6 show a preferred embodiment of a bottle which may be made out of mPP resins. The bottle preferably has a body with a neck. The body may be any suitable shape and preferably compliments the receiving portion of an electric warmer unit which will be used to dispense the fragrance oil in the bottle. A wick having a collar is inserted into the neck of the bottle as shown in phantom lines in FIG. 5. Examples of electric warmer units in which a mPP bottle of the invention is useful is described in U.S. Pat. No. 5,647,053 entitled "Vapor Dispensing Device", and U.S. Pat. No. 5,909,845 entitled "Wick-Based Liquid Emanation System With Child-Resistant Overcap", which are incorporated herein by reference. One such warmer unit device is commercially sold under the name Glade® PlugIns® by S. C. Johnson & Son, Inc., Racine, Wis.

Figure 7:
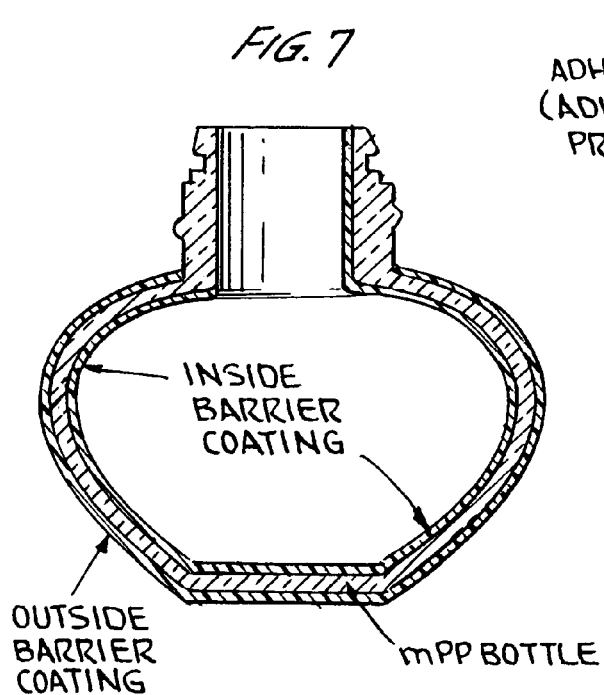
FIG. 7 shows a bottle of the invention made of mPP resin with a barrier coating on the inside and the outside of the bottle.

FIG. 7 shows a bottle made of mPP resin with a barrier coating on both the inside and outside of the bottle. The barrier coating can also be applied only on the inside or on the outside of the bottle as detailed above. Suitable barrier coating materials include Barex®, polyacrylonitrile (PAN), Nylon 6, Nylon 6-6, polyvinylidene chloride (PVDC), polyvinyl chloride (PVC), polyethylene naphthalene (PEN), polyethylene terephthalate (PET) or copolyesters sold by Eastman designated as glucolised polyethylene terephthalate (PETG), glucolised polycyclohexylenedimethylene terephthalate (PCTG) or pentachlorothioanisole(PCTA) or any material that could serve as an effective barrier coating layer to fragrance oils, or reduce the migration of oxygen, carbon dioxide or water vapor.

Figure 8:
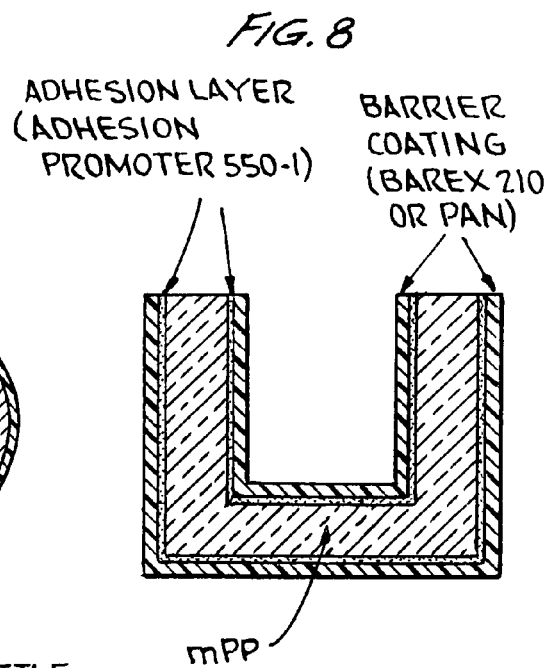
FIG. 8 illustrates schematically a cross-section of a bottle of the invention having an adhesive layer between the bottle material and a barrier coating.

FIG. 8 shows a schematic drawing of a bottle of the invention in cross-section showing the use of an adhesive layer between the bottle material and the barrier coating material as detailed above. For examplary purposes, the bottle in FIG. 8 is mPP, the adhesive layer is Eastman™ Adhesion Promoter 550-1, and the barrier coating is either Barex® 210 or polyacrylonitrile (PAN).

Although the present invention has been described in considerable detail, one skilled in the art will appreciate that the present invention can be practiced by other than the described embodiments, which have been presented for purposes of illustration and not of limitation. Therefore, the scope of the appended claims should not be limited to the description of the embodiments described herein.

It is claimed:

1. A bottle for holding and dispensing a fragrance oil composition in combination with a fragrance oil composition, said bottle comprising a body composed of metallocene polypropylene, and a barrier coating on an inside surface and/or an outside surface of said body, wherein said barrier coating comprises at least one of acrylonitrile methyl acrylate copolymer grafted onto nitrile rubber, polyacrylonitrile, Nylon 6, Nylon 6-6, polyvinylidene chloride, polyvinyl chloride, polyethylene naphthalene, polyethylene terephthalate, glucolised polyethylene terephthalate, glucolised polycyclohexylene-dimethylene terephthalate, or pentachlorothioanisole, wherein said metallocene polypropylene has a melt flow in a range from about 0.5 g/10 min. to about 50 g/10 min.

2. The bottle according to claim 1, wherein said metallocene polypropylene has a melt flow in a range from about 0.5 g/10 min. to about 40 g/10 min.

3. The bottle according to claim 1, wherein said metallocene polypropylene has a melt flow in a range from about 1 g/10 min. to about 20 g/10 min.

4. A bottle for holding and dispensing a fragrance oil composition in combination with a fragrance oil composition, said bottle comprising a body composed of metallocene polypropylene; a neck integral with said body and a wicking material positioned in said neck, said wicking material including a first portion at least partially disposed within said body and a second portion extending outside said body; and a barrier coating on an inside surface and/or an outside surface of said body, wherein said barrier coating includes at least one of acrylonitrile methyl acrylate copolymer grafted onto nitrile rubber, polyacrylonitrile, Nylon 6, Nylon 6-6, polyvinylidene chloride, polyvinyl chloride, polyethylene naphthalene, polyethylene terephthalate, glucolised polyethylene terephthalate, glucolised polycyclohexylenedimethylene terephthalate, or pentachlorothioanisole, wherein said metallocene polypropylene has a melt flow in a range from about 0.5 g/10 min. to about 50 g/10 min.

5. A bottle for holding and dispensing a fragrance oil composition in combination with a fragrance oil composition, said bottle comprising a body composed of metallocene polypropylene, wherein said bottle has been subjected to fluorination, wherein said metallocene polypropylene has a melt flow in a range from about 0.5 g/10 min. to about 50 g/10 min.

6. The bottle according to claim 5, wherein said metallocene polypropylene has a melt flow in a range from about 0.5 g/10 min. to about 40 g/10 min.

7. The bottle according to claim 5, wherein said metallocene polypropylene has a melt flow in a range from about 1 g/10 min. to about 20 g/10 min.

8. A bottle for holding and dispensing a fragrance oil composition in combination with a fragrance oil composition, said bottle comprising a body composed of metallocene polypropylene, a neck integral with said body and a wicking material positioned in said neck, said wicking material including a first portion at least partially disposed within said body and a second portion extending outside said body, wherein said bottle has been subjected to fluorination, wherein said metallocene polypropylene has a melt flow in a range from about 0.5 g/10 min. to about 50 g/10 min.

* * * * *